US011020589B2

(12) United States Patent
Syed et al.

(10) Patent No.: US 11,020,589 B2
(45) Date of Patent: Jun. 1, 2021

(54) MULTI-ELECTRODE EPICARDIAL PACING

(71) Applicants: Mayo Foundation for Medical Education and Research, Rochester, MN (US); St. Anne's University Hospital Brno, Brno (CZ)

(72) Inventors: Faisal F. Syed, Ann Arbor, MI (US); Charles J. Bruce, Rochester, MN (US); Christopher V. DeSimone, Rochester, MN (US); Paul A. Friedman, Rochester, MN (US); Samuel J. Asirvatham, Rochester, MN (US); Tomas Kara, Brno (CZ); Pavel Leinveber, Policka (CZ); Miroslav Novak, Brno (CZ); Zdenek Starek, Brno (CZ); Jiri Wolf, Nedakonice (CZ)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/366,754

(22) Filed: Mar. 27, 2019

(65) Prior Publication Data
US 2019/0224477 A1 Jul. 25, 2019

Related U.S. Application Data

(63) Continuation of application No. 15/119,893, filed as application No. PCT/US2015/021758 on Mar. 20, 2015, now Pat. No. 10,279,170.
(Continued)

(51) Int. Cl.
*A61N 1/05* (2006.01)
*A61N 1/362* (2006.01)
(Continued)

(52) U.S. Cl.
CPC ............ *A61N 1/0587* (2013.01); *A61B 18/14* (2013.01); *A61N 1/059* (2013.01); *A61N 1/0597* (2013.01);
(Continued)

(58) Field of Classification Search
CPC .. A61N 1/0587; A61N 1/39622; A61N 1/059; A61N 1/0597; A61N 1/3627;
(Continued)

(56) References Cited

U.S. PATENT DOCUMENTS 5,345,936 A 9/1994 Pomeranz et al.
5,462,544 A 10/1995 Saksena et al.
(Continued)

FOREIGN PATENT DOCUMENTS

WO WO2014018611 1/2014

OTHER PUBLICATIONS

Biffi et al., "Management of phrenic stimulation in CRT patients over the long term: still an unmet need?" Pacing Clin Electrophysiol., 34(10):1201-1208, Epub Jun. 8, 2011.
(Continued)

*Primary Examiner* — Paula J Stice
(74) *Attorney, Agent, or Firm* — Fish & Richardson P.C.

(57) ABSTRACT

Systems and methods for epicardial pacing are provided. For example, this document provides epicardial pacing using a percutaneously delivered bifurcated pacing lead that has multiple electrodes that are directionally insulated to prevent extracardiac stimulation, including prevention of phrenic stimulation. In addition, the devices, systems, and methods provided can be used for ablation, defibrillation, and/or defibrillation in combination with pacing.

14 Claims, 8 Drawing Sheets

Related U.S. Application Data (60) Provisional application No. 61/968,977, filed on Mar. 21, 2014.

(51) Int. Cl.
*A61B 18/14* (2006.01)
*A61N 1/39* (2006.01)
*A61N 1/372* (2006.01)
*A61B 18/00* (2006.01)

(52) U.S. Cl.
CPC ....... *A61N 1/3627* (2013.01); *A61N 1/39622* (2017.08); *A61B 18/1492* (2013.01); *A61B 2018/00279* (2013.01); *A61B 2018/00363* (2013.01); *A61B 2018/00577* (2013.01); *A61B 2018/1467* (2013.01); *A61N 1/37211* (2013.01)

(58) Field of Classification Search
CPC . A61N 1/37211; A61B 18/14; A61B 18/1492; A61B 2018/00297; A61B 2018/00393; A61B 2018/00577; A61B 2018/1467
See application file for complete search history.

(56) References Cited

U.S. PATENT DOCUMENTS

| | | | |
|---|---|---|---|
| 7,120,504 | B2 | 10/2006 | Osypka |
| 7,158,838 | B2 | 1/2007 | Seifert et al. |
| 7,463,932 | B2 | 12/2008 | Cawthra, Jr. |
| 7,515,969 | B2 | 4/2009 | Tockman et al. |
| 7,620,458 | B2 | 11/2009 | Friedman et al. |
| 7,920,928 | B1 | 4/2011 | Yang et al. |
| 8,036,757 | B2 | 10/2011 | Worley |
| 8,060,219 | B2 | 11/2011 | Ross et al. |
| 8,478,406 | B2 | 7/2013 | Burnes et al. |
| 8,548,603 | B2 | 10/2013 | Swoyer et al. |
| 8,606,355 | B1 | 12/2013 | Krause |
| 9,242,098 | B2 * | 1/2016 | Madjarov .......... A61B 18/1492 |
| 2004/0199236 | A1 * | 10/2004 | Laske ................ A61N 1/05 |
| 2005/0090870 | A1 | 4/2005 | Hine et al. |
| 2007/0156220 | A1 | 7/2007 | Kaplan et al. |
| 2007/0239247 | A1 | 10/2007 | Camps et al. |
| 2007/0293923 | A1 | 12/2007 | Soltis et al. |
| 2009/0299447 | A1 * | 12/2009 | Jensen ................ A61N 1/0587 607/130 |
| 2010/0241185 | A1 | 9/2010 | Mahapatra et al. |
| 2013/0131665 | A1 | 5/2013 | Wang et al. |
| 2013/0166007 | A1 | 6/2013 | True et al. |
| 2013/0253343 | A1 | 9/2013 | Waldhauser et al. |
| 2017/0056647 | A1 | 3/2017 | Syed et al. |

OTHER PUBLICATIONS

Biffi et al., "Occurrence of phrenic nerve stimulation in cardiac resynchronization therapy patients: the role of left ventricular lead type and placement site," Europace, 15(1):77-82, Epub Jul. 29, 2012, print Jan. 2013.

Biffi et al., "Phrenic stimulation management in CRT patients: are we there yet?" Curr Opin Cardiol., 26(1):12-6, Jan. 2011.

Biffi et al., "Phrenic stimulation: a challenge for cardiac resynchronization therapy," Circ Arrhythm Electrophysiol., 2(4):402-410, Epub Jun. 11, 2009.

Biffi et al., "Short-spaced dipole for managing phrenic nerve stimulation in patients with CRT: the "phrenic nerve mapping and stimulation EP" catheter study," Heart Rhythm, 10(1):39-45, Epub Sep. 1, 2012, Jan. 2013.

Bradley et al., "Cardiac resynchronization and death from progressive heart failure: a meta-analysis of randomized controlled trials," JAMA, 289(6):730-740, Feb. 12, 2003.

Brignole et al., "2013 ESC Guidelines on cardiac pacing and cardiac resynchronization therapy: the Task Force on cardiac pacing and resynchronization therapy of the European Society of Cardiology (ESC). Developed in collaboration with the European Heart Rhythm Association (EHRA)," Eur Heart J., 34(29):2281-329, Epub Jun. 24, 2013.

DeSimone et al., "Percutaneous autonomic neural modulation: a novel technique to treat cardiac arrhythmia," Cardiovasc Revasc Med., 14(3):144-148, Epub Apr. 29, 2013.

DeSimone et al., "Stroke or transient ischemic attack in patients with transvenous pacemaker or defibrillator and echocardiographically detected patent foramen ovale," Circulation, 128(13):1433-1441, Epub Aug. 14, 2013.

Epstein et al., "2012 ACCF/AHA/HRS focused update incorporated into the ACCF/AHA/HRS 2008 guidelines for device-based therapy of cardiac rhythm abnormalities: a report of the American College of Cardiology Foundation/American Heart Association Task Force on Practice Guidelines and the Heart Rhythm Society," J Am Coll Cardiol., 61(3):e6-75, print Jan. 22, 2013 Epub Dec. 19, 2012.

Goetze et al., "Phrenic nerve stimulation in CRT patients and benefits of electronic lead repositioning: the ERACE trial," J Interv Card Electrophysiol., 38(1):1-9, Epub Jul. 19, 2013.

Hjortshøj et al., "Long pacing pulses reduce phrenic nerve stimulation in left ventricular pacing," J Cardiovasc Electrophysiol., 25(5):485-490, Epub Jan. 6, 2014.

Hsia et al., "Novel minimally invasive, intrapericardial implantable cardioverter defibrillator coil system: a useful approach to arrhythmia therapy in children," Ann Thorac Surg., 87(4):1234-8; discussion 1238-1239, Apr. 2009.

Huizar et al., "Comparison of different pacing strategies to minimize phrenic nerve stimulation in cardiac resynchronization therapy," J Cardiovasc Electrophysiol., 24(9):1008-1014, Epub Apr. 26, 2013.

International Preliminary Report on Patentability for PCT/US2015/021758, dated Sep. 29, 2016, 9 pages.

International Search Report and Written Opinion for PCT/US2015/021758, dated Jul. 2, 2015, 17 pages.

Kondo et al., "Identification of left atrial ganglionated plexi by dense epicardial mapping as ablation targets for the treatment of concomitant atrial fibrillation," Pacing Clin Electrophysiol., 36(11):1336-1341, Epub Jun. 6, 2013.

Lachman et al., "Correlative anatomy for the electrophysiologist, Part I: the pericardial space, oblique sinus, transverse sinus," J Cardiovasc Electrophysiol., 21(12):1421-1426, Epub Aug. 19, 2010.

Lachman et al., "Correlative anatomy for the electrophysiologist, part II: cardiac ganglia, phrenic nerve, coronary venous system," J Cardiovasc Electrophysiol., 22(1):104-110, Epub Aug. 30, 2010.

McLeod et al., "Epicardial versus endocardial permanent pacing in adults with congenital heart disease," J Interv Card Electrophysiol., 28(3):235-243, Epub Jun. 19, 2010.

Mizuno et al., "The utility of manually controlled steerable sheath in epicardial mapping and ablation procedure in patients with ventricular tachycardia," Europace, 14 Suppl 2:ii19-ii23, Aug. 2012.

Na et al., "Unidirectional ablation electrode to minimize thermal injury during radiofrequency ablation: an experimental study in an ex vivo bovine liver model," J Vasc Interv Radiol., 22(7):935-940, Epub May 6, 2011.

Ota et al., "Subxiphoid epicardial left ventricular pacing lead placement is feasible," J Thorac Cardiovasc Surg., 139(6):1661-2. Epub Oct. 8, 2009, print Jun. 2010.

Ploux et al., "Acute electrical and hemodynamic effects of multisite left ventricular pacing for cardiac resynchronization therapy in the dyssynchronous canine heart," Heart Rhythm., 11(1):119-125, Epub Oct. 9, 2013, print Jan. 11, 2014.

Sangaralingham et al., "Rationale and design of a randomized, double-blind, placebo-controlled clinical trial to evaluate the efficacy of B-type natriuretic peptide for the preservation of left ventricular function after anterior myocardial infarction," J Card Fail., 19(8):533-539, Aug. 2013.

Sosa et al., "A new technique to perform epicardial mapping in the electrophysiology laboratory," J Cardiovasc Electrophysiol., 7(6):531-536, Jun. 1996.

Syed et al., "Percutaneous Epicardial Pacing using a Novel Insulated Multi-electrode Lead," JACC Clin Electrophysiol., 1(4):273-283, Aug. 2015.

(56) References Cited

OTHER PUBLICATIONS

Syed et al., "The Pericardial Space: Obtaining Access and an Approach to Fluoroscopic Anatomy," Cardiac Electrophysiology Clinics., 2:9-23, 2010.
Syed, "Percutaneous Epicardial Pacing Using a Novel Partially Insulated Multi-electrode Lead," Heart Rhythm J, 11(5):Supplement, S551, Abstract YIA-04, May 2014, 1 page.
Syed, "Percutaneous Epicardial Pacing Using a Novel Partially Insulated Multi-electrode Lead," Heart Rhythm Society Meeting, May 8, 2014, 41 slides.
Syed, "Percutaneous Epicardial Pacing Using a Novel Partially Insulated Multi-electrode Lead," Mayo Clinic Young Investigator Research Symposium, Mar. 22-23, 2014, 1 poster.
Zenati et al., "Left heart pacing lead implantation using subxiphoid videopericardioscopy," J Cardiovasc Electrophysiol., 14(9):949-953, Sep. 2003.

\* cited by examiner

MULTI-ELECTRODE EPICARDIAL PACING

CROSS-REFERENCE TO RELATED APPLICATIONS

This application is a continuation of U.S. application Ser. No. 15/119,893, now U.S. Pat. No. 10,279,170, filed Aug. 18, 2016, which is a U.S. National Stage under 35 U.S.C. § 371 of International Application No. PCT/US2015/021758, filed Mar. 20, 2015, which claims the benefit of U.S. Provisional Application Ser. No. 61/968,977, filed Mar. 21, 2014. The disclosure of the prior applications are considered part of (and are incorporated by reference in) the disclosure of this application.

BACKGROUND

1. Technical Field

This document relates to systems and methods for epicardial pacing, ablation, and defibrillation. For example, some embodiments provided in this document relate to epicardial pacing using a percutaneously delivered bifurcated pacing lead that has multiple electrodes that are directionally insulated to prevent extracardiac stimulation.

2. Background Information

Cardiac resynchronization therapy (CRT) results in a significant reduction in mortality and symptoms in selected patients with heart failure. In some cases, temporary pacing using an epicardial approach is undertaken to treat dysrhythmias and to improve hemodynamics in selected patients with heart failure. Using the epicardial approach to pacing lead placement, an implanted pacing lead forms a direct current path to the myocardium. A pulse generator or pacemaker provides electrical field stimuli to the myocardium via one or more electrodes located on the pacing lead and in contact with the myocardium.

With 2% of the adult population in the developed world currently suffering from heart failure, a rising prevalence as longevity increases, and an estimated 5-10% of heart failure patients having an indication for CRT, there is an increasing role for versatile pacing approaches.

SUMMARY

This document provides systems and methods for epicardial pacing, ablation, and defibrillation. For example, this document provides epicardial pacing using a percutaneously delivered bifurcated pacing lead that has multiple electrodes that are directionally insulated to prevent extracardiac stimulation, including prevention of phrenic stimulation.

In general, one aspect of this document features an epicardial pacing lead device. The epicardial pacing lead device comprises a first shaft having one or more electrodes disposed thereon and a second shaft having one or more electrodes disposed thereon. At least some of the electrodes are insulated so as to substantially inhibit emanation of electrical fields therefrom in a particular direction corresponding to the location at which the electrodes are insulated.

Such epicardial pacing lead devices can optionally include one or more of the following features. The first shaft and the second shaft may have the same number of electrodes. The epicardial pacing electrode may be configured to be a bipolar epicardial pacing electrode. The first shaft and the second shaft may be configured for transcatheter deployment. One or more of the electrodes that are insulated may be each insulated so as to substantially inhibit emanation of electrical fields therefrom in the same direction. The first shaft and the second shaft may be distinctly separate distal end portions extending from a common shaft such that the separate distal end portions and the common shaft comprise a Y-shape. Distal end portions of the first shaft and the second shaft may be interconnected by a flexible elongate spacing member. The flexible elongate spacing member may be configured to be extendable and retractable, and extending and retracting the flexible elongate member may change the spacing between the first shaft and the second shaft. The flexible elongate spacing member may be a first flexible elongate spacing member, and the epicardial pacing lead device may further comprise a second flexible elongate spacing member interconnecting the first shaft and the second shaft. The second flexible member may be located proximally of the first elongate spacing member. the epicardial pacing lead device may further comprise a stabilization member interconnecting the first shaft and the second shaft. The stabilization member may project away from a plane defined by the first shaft in combination with the second shaft. The epicardial pacing lead device may be configured for performance of ablation or defibrillation.

In a second general aspect, this document features an epicardial pacing device system. The epicardial pacing device system comprises an epicardial pacing lead device comprising a first shaft having one or more electrodes disposed thereon, wherein at least some of the electrodes are insulated so as to substantially inhibit emanation of electrical fields therefrom in a particular direction corresponding to the location at which the electrodes are insulated; and a delivery sheath, wherein a first lumen of the delivery sheath is configured to slidably receive the epicardial pacing electrode.

Such epicardial pacing device systems may optionally include one or more of the following features. The epicardial pacing lead device may further comprise a second shaft having one or more electrodes disposed thereon. At least a distal end portion of the delivery may be steerable. At least a distal end of the first shaft may be steerable. The delivery sheath or the first shaft may include a lumen therethrough that is configured for aspiration or irrigation. The epicardial pacing device system may further comprise an anchorage device that is configured to be slidably deliverable through a second lumen of the delivery sheath. The epicardial pacing lead device may be configured for performance of ablation or defibrillation. The epicardial pacing lead device may include at least one aperture between two adjacent electrodes of the one or more electrodes, and the system may further comprise an imaging catheter that is configured to performing imaging through the at least one aperture.

In a third general aspect, this document features a method for epicardial pacing of a heart of a human patient. The method comprises (1) percutaneously inserting a delivery sheath into the patient and navigating a distal end portion of the delivery sheath to within a pericardial sac of the patient; (2) deploying an epicardial pacing lead device through a first lumen of the delivery sheath, the epicardial pacing lead device comprising a first shaft having one or more electrodes disposed thereon, wherein at least some of the electrodes are insulated so as to substantially inhibit emanation of electrical fields therefrom in a particular direction corresponding to the location at which the electrodes are insulated; (3) orienting the epicardial pacing lead device so that the one or more electrodes at least partially contact myocardium of the patient; and (4) activating a source of electrical energy to provide pacing energy to the myocardium of the heart via the one or more electrodes, wherein the insulation of the electrodes substantially inhibits extracardiac stimulation.

Such methods for epicardial pacing of a heart of a human patient may optionally include one or more of the following features. The epicardial pacing lead device may further comprise a second shaft having one or more electrodes disposed thereon. The epicardial pacing lead device may be configured for performance of ablation or defibrillation, and the method may be performed for ablation or defibrillation.

Particular embodiments of the subject matter described in this document can be implemented to realize one or more of the following advantages. In some embodiments, heart conditions such as heart failure, fibrillation, and others can be treated using the systems and methods provided herein. In some embodiments, pacing stimuli can be delivered to the myocardium while preventing extracardiac stimulation, including prevention of phrenic stimulation. Some embodiments of the pacing leads provided herein are configured to utilize the pericardium for mechanical support, and may include additional design features to provide enhanced lead stability and anti-migration. In some embodiments, various heart conditions can be treated in a minimally invasive percutaneous fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides systems and methods for epicardial pacing, ablation, and defibrillation. For example, this document provides epicardial pacing systems using a percutaneously delivered bifurcated pacing lead that has multiple electrodes that are directionally insulated to prevent extracardiac stimulation, including prevention of phrenic stimulation.

The devices and systems provided herein may also be used for other heart treatment modalities. For example, in some embodiments the devices and systems provided herein can be used to perform bipolar or unipolar full-thickness ablation from the epicardium to the endocardium. In some such embodiments, magnetic coupling is used between the ablation instruments to facilitate alignment of the instruments for efficient ablation. Also, in some such embodiments suction can be used to selectively anchor one ablation instrument on the epicardium while the other ablation instrument within the heart is magnetically aligned or visually aligned to the instrument on the epicardium. In another example, some embodiments of the pacing lead designs provided herein can be used to stimulate the phrenic nerve to treat central sleep apnea.

Additional example treatment modalities using some embodiments of the devices and methods provided herein include, but are not limited to: defibrillation; mapping of accessory pathways and ventricular tachycardia (VT) circuits (in addition to ablation); targeted interrogation and ablation of the autonomic ganglia and cardiac nerves as modulators of arrhythmia; appendage pacing for thrombosis prevention; coronary vascular intervention for revascularization strategies such as aiding endovascular approaches to chronic total occlusion (CTO) stenting; biological therapies such as to perivascular adventitia to modulate the vessel wall; coronary vascular intervention for revascularization strategies including aiding endovascular approaches to CTO stenting, and biological therapies for vasospasm; cardiac contractility modulation; monitoring of cardiac autonomic activity; and non-cardiac applications including ablation of: liver lesions, bladder lesions, CNS lesions (via a burr hole), pancreatic lesions, and intestinal lesions. In some embodiments, steroid solutions (and/or other pharmacological agents) can be delivered in conjunction with the pacing leads to enhance the operation of the devices and methods provided herein. Still other advantageous implementations and adaptations of the devices and methods provided herein are also envisioned.

Figure 1:
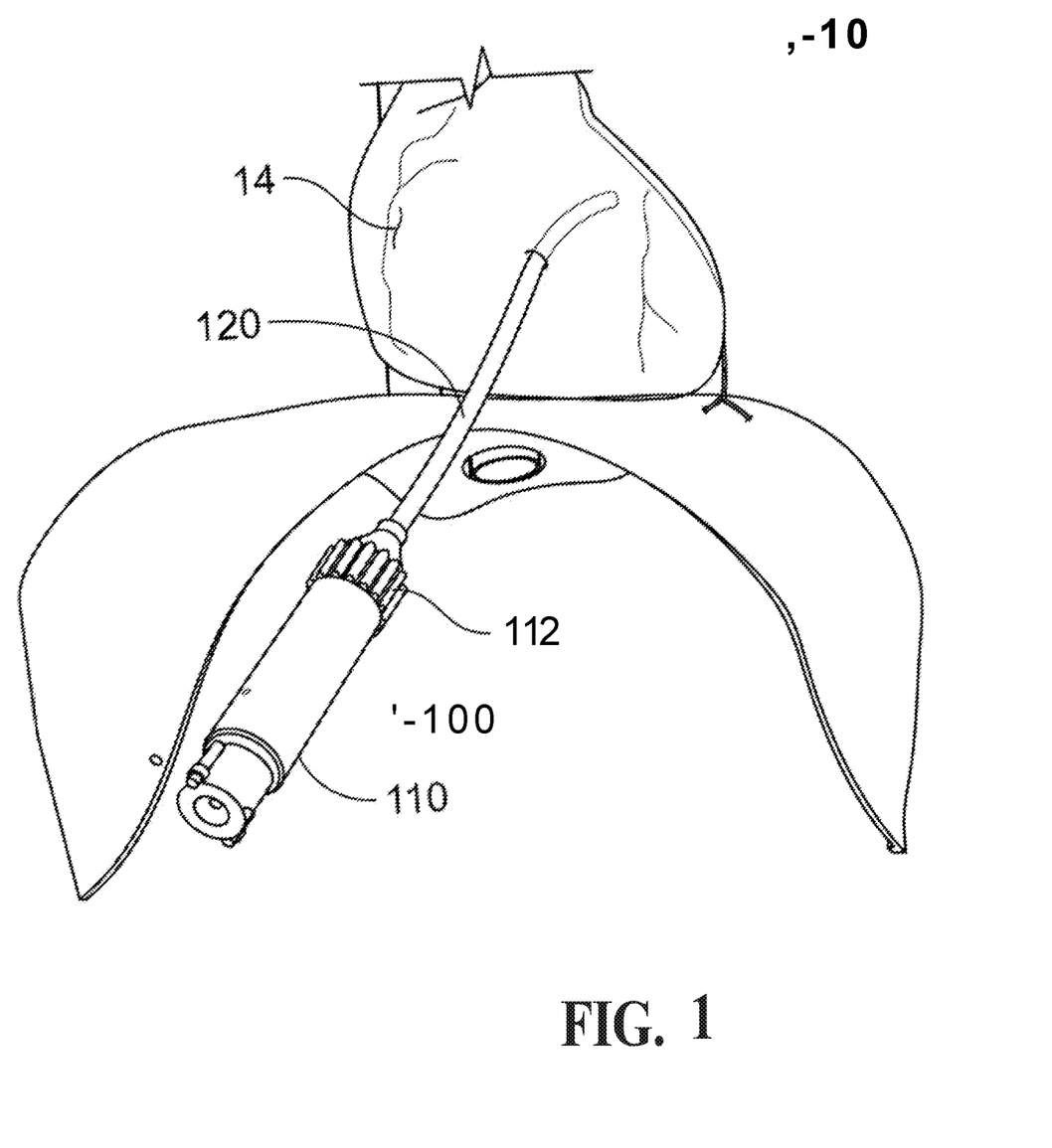
FIG. 1 is a perspective diagram of a percutaneous pacing lead placement procedure using a steerable catheter-based delivery device in accordance with some embodiments provided herein.

With reference to FIG. 1, a percutaneous pacing lead delivery system 100 includes a handle 110 and a steerable sheath 120. Percutaneous pacing lead delivery system 100 is configured to deliver one or more epicardial pacing leads to a target location within a pericardial sac 14 of a heart 10 (as will be described further below).

Steerable sheath 120 extends distally from handle 110. Handle 110 is configured to remain exterior of the patient, while at least portions of steerable sheath 120 are configured to extend percutaneously into the interior regions of the patient's body including into pericardial sac 14 of heart 10.

In some embodiments, one or more actuators such as actuator 112 are disposed on handle 110. For example, actuator 112 can be manipulated by a clinician operator to steer at least a distal end portion of steerable sheath 120. By such steering, the clinician operator can deliver one or more pacing leads to a target location in relation to heart 10. In some embodiments, more than one actuator 112 is included in delivery system 100. For example, additional actuators 112 may be included to facilitate manipulation of other features of some embodiments of pacing lead(s), such as stability features and anchorage features as described further below.

In some embodiments, one or more radiopaque markers are included on at least the distal end portion of steerable sheath 120. In some such embodiments, the placement of the radiopaque markers on the distal end portion of steerable sheath 120 can indicate the orientation of the pacing electrodes located within steerable sheath 120. Accordingly, in some implementations x-ray fluoroscopy can be used to assist the clinician operator with placing steerable sheath 120, and the pacing electrodes therein, in an intended orientation in relation to the heart 10. In some implementations, other imaging modalities can be used in combination with, or as an alternative to, fluoroscopy. Such imaging modalities can include, but are not limited to, echo navigation (including 3D transesophageal echocardiography (TEE)), spectroscopic photoacoustic microscopy, and others.

In some implementations, percutaneous pacing lead delivery system 100 is used for percutaneous access to heart 10, including, for example, subxiphoid access to the pericardial space of heart 10. Much of the cardiac surface is reachable through such an anterior approach. In some implementations, the placement of the pacing lead(s) can be in locations on heart 10 such as, but not limited to, over the right ventricular outflow tract (RVOT), the anterolateral left ventricular free wall (LV), or the left atrial appendage (LAA). In some implementations, other approaches to heart 10 including, but not limited to, various minimally-invasive approaches, thoracotomy, subcostal or intercostal approaches can be used.

In some embodiments, steerable sheath 120 includes one or more lumens therethrough. For example, in some embodiments steerable sheath 120 includes one or more lumens for passing the pacing electrodes therethrough. In some embodiments, steerable sheath 120 includes one or more other lumens for aspiration or irrigation. In some embodiments, steerable sheath 120 includes one or more other lumens for other devices such as, but not limited to, stability devices, ultrasonic imaging devices, sensors, and/or other devices.

In some embodiments, steerable sheath 120 has a circular cross-sectional shape. In some embodiments, steerable sheath 120 has a non-circular cross-sectional shape. For example, in some embodiments steerable sheath 120 is ovular, triangular, multi-lobed, or otherwise non-circular.

Figure 2A:
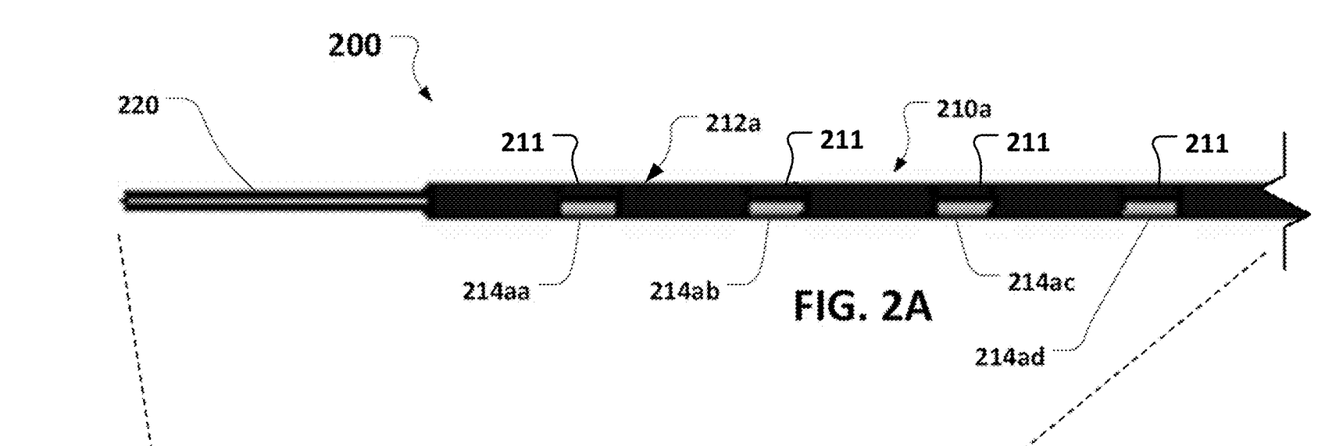
FIG. 2A is a side view of a distal end portion of an example bifurcated multi-electrode pacing lead in accordance with some embodiments provided herein.
Figure 2B:
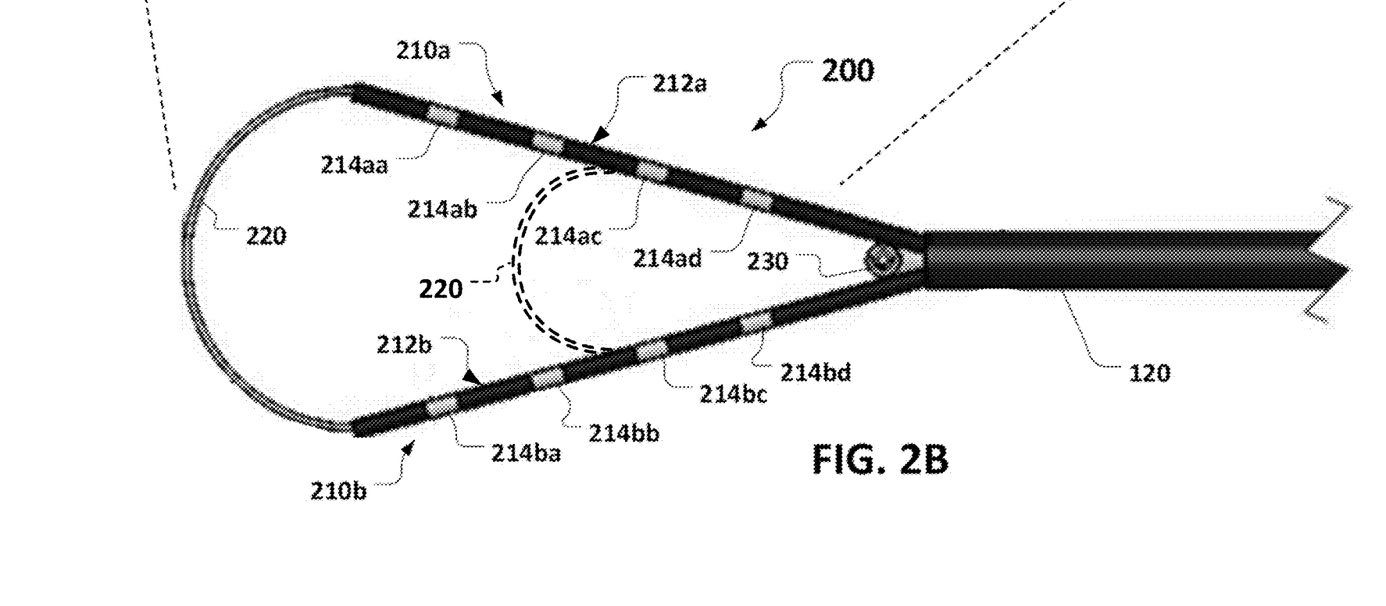
FIG. 2B is a plan view of the distal end portion of the example bifurcated multi-electrode pacing lead of FIG. 2A.

With reference to FIGS. 2A and 2B, an example bifurcated multi-electrode pacing lead 200 can include a first pacing lead 210a and a second pacing lead 210b. Bifurcated multi-electrode pacing lead 200 can be delivered to a target location via steerable sheath 120. It should be understood that, while this device is described in the context of pacing, this device can also be used for other purposes including, but not limited to, ablation, defibrillation, and a combination of pacing and defibrillation. In some embodiments, pacing lead 200 can be used for atrial-ventricular pacing, multi-site ventricular pacing, or biventricular pacing for CRT.

In some embodiments, first pacing lead 210a and second pacing lead 210b are separate shafts that are individually slidably disposed within one or more lumens of sheath 120 and are configured to be partially extendable beyond the distal end of sheath 120. In some such embodiments, first pacing lead 210a and second pacing lead 210b can be configured symmetrically in relation to each other. However, in some such embodiments first pacing lead 210a and second pacing lead 210b can be configured asymmetrically in relation to each other. For example, in some embodiments one of either first pacing lead 210a or second pacing lead 210b can be extended further from the end of delivery sheath 120 than the other of first pacing lead 210a or second pacing lead 210b.

In some embodiments, proximal portions of first pacing lead 210a and second pacing lead 210b are a unified shaft, and distal portions of first pacing lead 210a and second pacing lead 210b are separate shafts (e.g., bifurcated). That is, in some embodiments distal end portions of first pacing lead 210a and second pacing lead 210b are separate and are conjoined at a junction that is proximal of the distal end portions (e.g., to form the shape of a "Y"). While the depicted embodiment includes two (2) pacing leads 210a and 210b, in some embodiments more than two (2) pacing leads are included in the device. For example, some embodiments include three, four, or more than four pacing leads.

First pacing lead 210a includes a first shaft 212a and one or more electrodes 214aa, 214ab, 214ac, and 214ad that are discretely disposed apart from each other on first shaft 212a. Second pacing lead 210b includes a second shaft 212b and one or more electrodes 214ba, 214bb, 214bc, and 214bd that are discretely disposed apart from each other on second shaft 212b. While the depicted embodiment includes four (4) electrodes on each pacing lead 210a-b, in some embodiments fewer or more than four (4) electrodes are included. In some embodiments, first shaft 212a and/or second shaft 212b can include one or more apertures. In some such embodiments, apertures can be within electrodes or near to electrodes. Such apertures can be confluent with one or more lumens that are defined within first shaft 212a and/or second shaft 212b. Accordingly, in some such embodiments suction can be applied via the one or more lumens and apertures for various purposes including, but not limited to, selective anchorage of first shaft 212a and/or second shaft 212b to target tissue (e.g., epicardial tissue), aspiration, and the like. Such anchorage of first shaft 212a and/or second shaft 212b to target tissue can also be used in conjunction with imaging systems to confirm a desired orientation of first shaft 212a and/or second shaft 212b in relation to target tissue.

In some embodiments, first shaft 212a and second shaft 212b are about 1.5 mm in diameter. In some embodiments, first shaft 212a and second shaft 212b are smaller or larger than 1.5 mm in diameter. The electrodes 214aa, 214ab, 214*ac*, 214*ad*, 214*ba*, 214*bb*, 214*bc*, and 214*bd* are about 3.2 mm long in some embodiments. However, in other embodiments, the 214*aa*, 214*ab*, 214*ac*, 214*ad*, 214*ba*, 214*bb*, 214*bc*, and 214*bd* can be longer or shorter than 3.2 mm. In some embodiments, the spacing between adjacent electrodes is about 10 mm center-to-center. However, in other embodiments spaces longer or shorter than 10 mm center-to-center between adjacent electrodes are used.

It should be understood that, while electrodes 214*aa*, 214*ab*, 214*ac*, 214*ad*, 214*ba*, 214*bb*, 214*bc*, and 214*bd* are depicted as cylindrical segments that are generally flush with outer diameters of first shaft 212*a* or second shaft 212*b*, such a configuration of the electrodes is not required. For example, in some embodiments one or more of the electrodes project radially from the shaft rather than being flush therewith. Further, other electrode shapes are envisioned. For example, in some embodiments one or more of the electrodes are concaved to generally conform to the surface contours of the epicardial tissue. In some embodiments, the concaved shape of the electrodes can be used advantageously to carry a conductive gel material to enhance the electrical conductivity between the electrode and the epicardial tissue.

In some embodiments, the electrodes 214*aa*, 214*ab*, 214*ac*, 214*ad*, 214*ba*, 214*bb*, 214*bc*, and 214*bd* can be selectively configured to operate as bipolar pairs. That is, for example, 214*aa* and 214*ba* can be a bipolar pair; 214*ab* and 214*bb* can be a bipolar pair; 214*ac* and 214*bc* can be a bipolar pair; and 214*ad* and 214*bd* can be a bipolar pair. However, in some embodiments, other bipolar pair arrangements can be selectively established, or monopolar electrodes can be used. In some embodiments, the electrodes on a single shaft can be paired as a bipolar pair. For example, electrodes 214*aa* and 214*ab* can be a bipolar pair; 214*ac* and 214*ad* can be a bipolar pair; and so on. In some embodiments, multiple electrodes are electrically coupled to functionally act as a single larger surface electrode. For example, in some embodiments all the electrodes on a shaft can functionally act as a single electrode. Such a configuration can be advantageously used for monopolar pacing in some implementations. Such a configuration can also be used to make multiple electrodes act as a return electrode for endocardial ablation, or to diminish impedance with bipolar epicardial ablation.

In some embodiments, one or more of electrodes 214*aa*, 214*ab*, 214*ac*, 214*ad*, 214*ba*, 214*bb*, 214*bc*, and 214*bd* are selectively movable in relation to first shaft 212*a* or second shaft 212*b*. For example, in some embodiments one or more of electrodes 214*aa*, 214*ab*, 214*ac*, 214*ad*, 214*ba*, 214*bb*, 214*bc*, and 214*bd* can be translated and/or rotated in relation to first shaft 212*a* or second shaft 212*b* into positions as desired.

In some embodiments, first pacing lead 210*a* and second pacing lead 210*b* can include electrical insulation material 211 near or on electrodes 214*aa*, 214*ab*, 214*ac*, 214*ad*, 214*ba*, 214*bb*, 214*bc*, and 214*bd* so that the electrical fields emanating from 214*aa*, 214*ab*, 214*ac*, 214*ad*, 214*ba*, 214*bb*, 214*bc*, and 214*bd* are directional. That is, in some embodiments electrodes 214*aa*, 214*ab*, 214*ac*, 214*ad*, 214*ba*, 214*bb*, 214*bc*, and 214*bd* have about 180° of exposed electrode surface, and the exposed electrode surfaces are oriented in relation to first shaft 212*a* and second shaft 212*b* so that electrical fields for pacing emanate in a desired direction (e.g., a downward direction in reference to FIG. 2A, or towards myocardium in reference to FIG. 4). In some embodiments, the exposed surfaces of electrodes 214*aa*, 214*ab*, 214*ac*, 214*ad*, 214*ba*, 214*bb*, 214*bc*, and 214*bd* are greater than or less than 180°. The insulation material 211 can include, but is not limited to, Pebax®, other nylons, silicone, and the like. In some embodiments, the insulation material 211 is adjustable, in situ, in relation to the amount of exposed conductive electrode surface. For example, in some embodiments at least a portion of the insulation material 211 on one or more of the electrodes is movable by a clinician operator so as to adjustably reveal or conceal a desired surface area of the electrodes. In some such embodiments, the clinician may configure the insulation material 211 to substantially completely cover the electrodes during deployment of the pacing lead. Thereafter, the clinician can reconfigure the position of the insulation material 211 in relation to the electrodes as desired, so as to reveal a desired area of electrode surface.

One or more radiopaque markers (or other fiducial markers, including but not limited to, echogenic material and other types of elements/materials visible by imaging systems) can be included on first pacing lead 210*a* and/or second pacing lead 210*b* in some embodiments. The one or more radiopaque markers can be positioned on first pacing lead 210*a* and/or second pacing lead 210*b* so as to indicate to a clinician operator the orientation of first pacing lead 210*a* and second pacing lead 210*b*, including the directional orientation of electrodes 214*aa*, 214*ab*, 214*ac*, 214*ad*, 214*ba*, 214*bb*, 214*bc*, and 214*bd*.

In some embodiments, first pacing lead 210*a* and second pacing lead 210*b* are actively steerable (e.g., via magnetic field or mechanical deflection). In some embodiments, first pacing lead 210*a* and second pacing lead 210*b* are inherently curved to a convexity similar to the contours of the epicardial surface, to facilitate contact integrity therebetween. In some embodiments, at least the distal end portions of first pacing lead 210*a* and second pacing lead 210*b* are malleable (or include malleable portions) such that a clinician can induce first pacing lead 210*a* and second pacing lead 210*b* to be shaped with a desired contour.

In some embodiments, first shaft 212*a* and/or second shaft 212*b* have one or more lumens therethrough. For example, in some embodiments first pacing lead 210*a* and second pacing lead 210*b* are interconnected by an elongate flexible spacing member 220 that is slidably disposed in lumens of one or both of first pacing lead 210*a* and second pacing lead 210*b*. In some embodiments, elongate flexible spacing member 220 is a wire, such as a nitinol wire. For example, in some embodiments elongate flexible spacing member 220 is a 0.5 mm diameter nitinol wire. In other embodiments, other sizes of nitinol wire and/or other types of materials can be used as elongate flexible spacing member 220.

In some embodiments, one or more thermistors or other types of temperature sensors are included on either or both of first pacing lead 210*a* and second pacing lead 210*b*. Such thermistors can be used to monitor tissue temperatures.

While in the depicted embodiment spacing member 220 extends between the extreme distal ends of first shaft 212*a* and second shaft 212*b*, in some embodiments spacing member 220 is positioned between first shaft 212*a* and second shaft 212*b* at various other locations that are not at the extreme distal ends thereof (e.g., as depicted by the spacing member 220 drawn in broken lines in FIG. 2B). That is, in some embodiments spacing member 220 extends between first shaft 212*a* and second shaft 212*b* at locations proximal of the extreme distal ends, such as near the midpoints of first shaft 212*a* and second shaft 212*b*, for example. Other locations are also envisioned. In some embodiments, more than one spacing member 220 is included. For example, two or more spacing members 220 at different locations between first shaft 212a and second shaft 212b can be included in some embodiments (e.g., as depicted in FIG. 2B by: (i) the spacing member 220 extending between the extreme distal ends of first shaft 212a and second shaft 212b and (ii) the spacing member 220 drawn in broken lines).

In some embodiments, one or more electrodes are included on the one or more spacing members 220.

In some embodiments, example bifurcated multi-electrode pacing lead 200 can include one or more of an ancillary device 230. Ancillary device 230 can selectively attach pacing lead 200 to target tissue. In some embodiments, ancillary device 230 is a suction device. In some embodiments, ancillary device 230 is an anchorage element such as, but not limited to, a helical coil, a barb, a radiused needle, a clamp, and the like. While in the depicted embodiment, ancillary device 230 is located near the junction of first shaft 212a and second shaft 212b, in some embodiments one or more ancillary devices 230 are located at other positions along first shaft 212a and second shaft 212b, including at the distal ends of first shaft 212a and second shaft 212b in some embodiments.

While in the depicted embodiment a single ancillary device 230 is included, in some embodiments two or more ancillary devices 230 are included. For example, in some embodiments a first ancillary device 230 is located as shown, a second ancillary device 230 is attached to first shaft 212a, and a third ancillary device 230 is attached to the second shaft 212b. The second and third ancillary devices 230 can be located at any locations along the first and second shafts 212a and 212b. In another example embodiment, no ancillary device 230 is located near the junction of first shaft 212a and second shaft 212b (as shown). Rather a first ancillary device 230 is attached to first shaft 212a, and a second ancillary device 230 is attached to second shaft 212b. It should be understood that the preceding examples are non-limiting. Other arrangements of one or more ancillary devices 230 relative to bifurcated multi-electrode pacing lead 200 are also envisioned and within the scope of this disclosure.

Figure 2C:
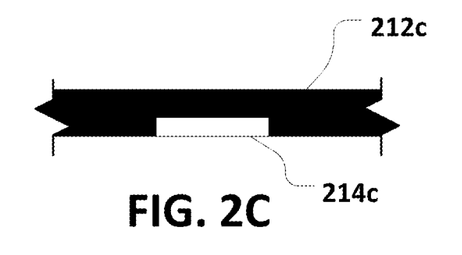
FIGS. 2C and 2D are side and plan views of an example electrode on a portion of a shaft.
Figure 2D:
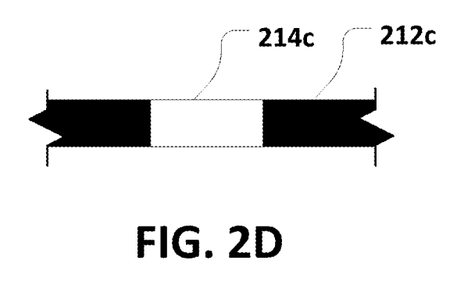

With reference to FIGS. 2C and 2D, an example electrode 214c on a shaft 212c has about an 180° exposed (non-insulated) electrode surface. FIG. 2C provides a side view of such an electrode 214c, and FIG. 2D provides a plan view of such an electrode 214c. However, it should be understood that an exposed surface of 180° is not required in all embodiments.

Figure 2E:
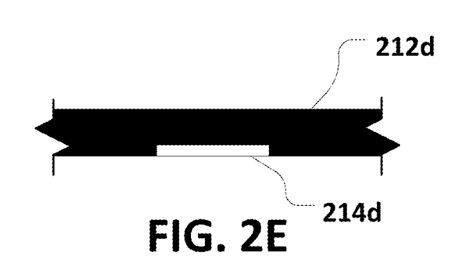
FIGS. 2E and 2F are side and plan views of another example electrode on a portion of a shaft.
Figure 2F:
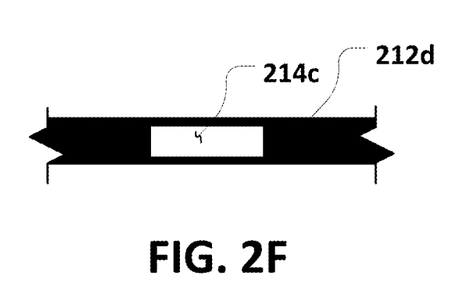

With reference to FIGS. 2E and 2F, another electrode 214d on a shaft 212d has about an 135° exposed (non-insulated) electrode surface. FIG. 2E provides a side view of such an electrode 214d, and FIG. 2F provides a plan view of such an electrode 214d. Therefore, it should be understood that electrodes included on the devices provided herein can have various amounts of exposed electrode surface, including amounts lesser than 135° and greater than 180° in some embodiments.

Figure 3A:
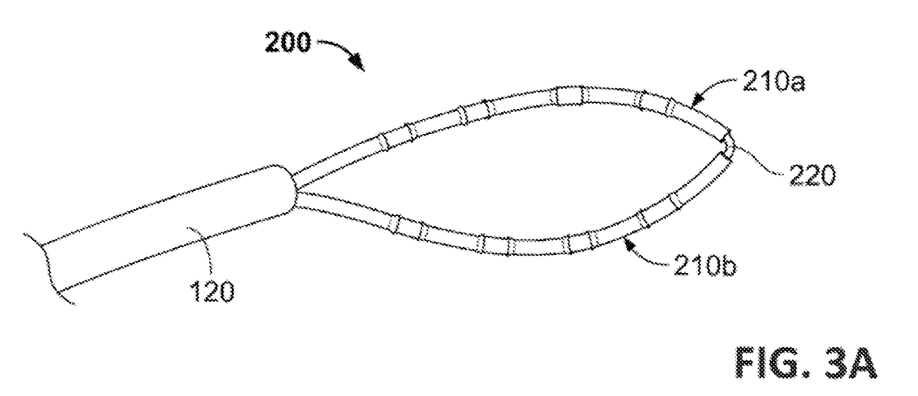
FIGS. 3A-3C are additional views of the pacing lead of FIG. 2 showing various configurations that the pacing lead can be manipulated to have.
Figure 3B:
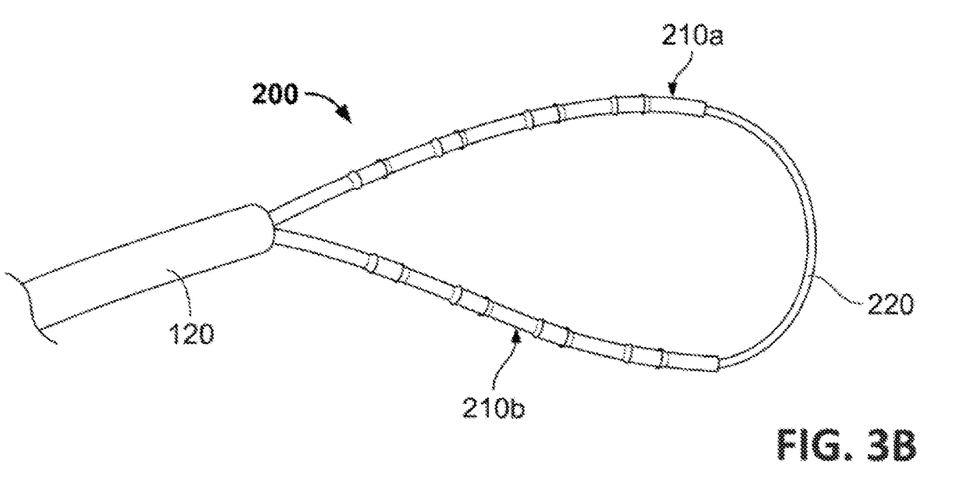

With reference to FIGS. 3A and 3B, in some embodiments, elongate flexible spacing member 220 can be movable in relation to first pacing lead 210a and second pacing lead 210b so as to affect the relative configurations of first pacing lead 210a and second pacing lead 210b. For example, in some embodiments a clinician operator can apply tension to elongate flexible spacing member 220 so as to draw first pacing lead 210a and second pacing lead 210b towards each other as shown in FIG. 3A. Conversely, in some embodiments the clinician operator can extend elongate flexible spacing member 220 so as to separate first pacing lead 210a and second pacing lead 210b away from each other as shown in FIG. 3B. In some embodiments, when elongate flexible spacing member 220 is extended, the distal ends of first pacing lead 210a and second pacing lead 210b are spaced apart from each other by about 10 mm or more. However, such spacing is adjustable to other lesser or greater distances as desired to suit the particular implementation. In some embodiments, the arms are articulable by a clinician so as to adjust the distance between them, and to match the curved contour of the epicardial surface.

Figure 3C:
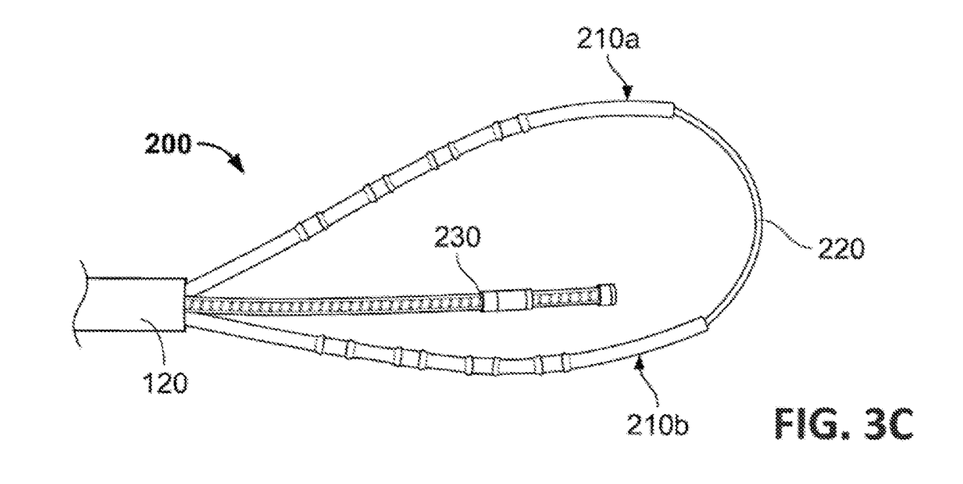

With reference to FIG. 3C, in some embodiments steerable sheath 120 can be used to deliver one or more additional devices therethrough. For example, an ancillary device 230 can be slidably delivered through sheath 120 such that a distal portion of ancillary device 230 extends from the distal end of sheath 120.

Ancillary device 230 can be many different types of devices and combinations of devices. In some such embodiments, ancillary device 230 includes an anchoring member such as, but not limited to, a coil that can be selectively extended and rotated from the distal end of ancillary device 230, so that it can penetrate into tissue, such as myocardial tissue. In that fashion, ancillary device 230 can be used to prevent or inhibit migration of bifurcated multi-electrode pacing lead 200. In some such embodiments, the anchoring member can engage with spacing member 220 to anchor spacing member 220 to tissue. In another example, instead of a coil anchoring member, the anchoring member can be a deployable wire/nitinol hook that captures epicardial tissue at a pre-determined depth, or alternatively, be designed to capture parietal pericardium. In some embodiments, ancillary device 230 can be a unipolar or bipolar pacing lead (as illustrated) that is extendible from delivery sheath 120 to permit independent sensing and pacing of the atrium while the other lead(s) pace and sense the ventricle. In some embodiments, ancillary device 230 is a combination of such devices, and other like devices. For example, ancillary device 230 can be both a pacing lead and include an anchoring member. Ancillary device 230 can also be many other types of devices. For instance, in another example ancillary device 230 can be a defibrillation coil. Ancillary device 230 can be extended from delivery sheath 120 to various extents, as desired.

Figure 4:
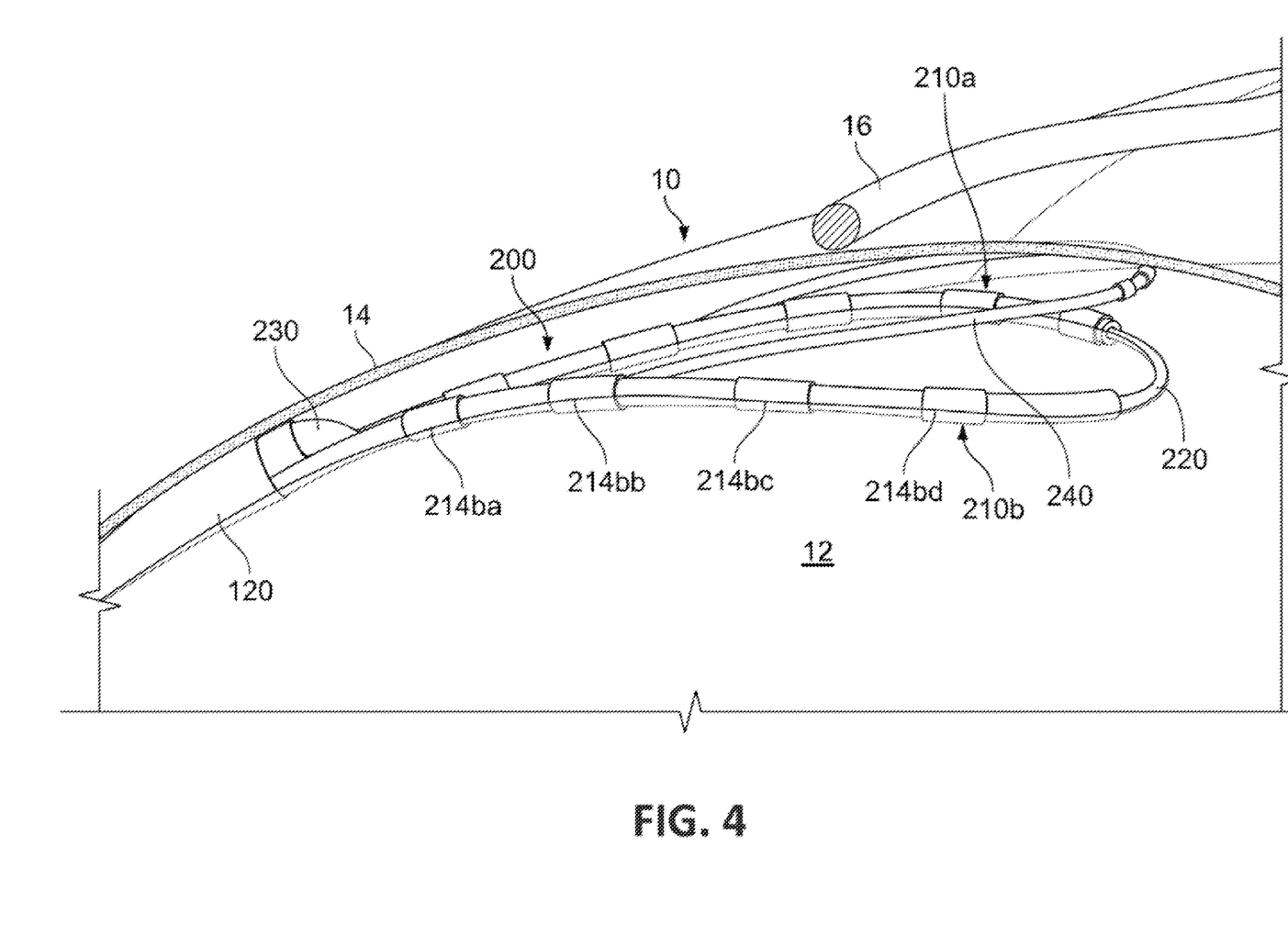
FIG. 4 is a perspective cutaway view of a pacing lead positioned within the pericardial sac such that the electrodes of the pacing lead are in contact with myocardial tissue.

In some embodiments, spacing member 220 includes selectively deployable, stabilizing barbs for anchoring. Additionally, two or more spacing members 220 can be included. For example, in some embodiments dual spacing members 220 are included. One of the spacing members 220 can be used to establish and maintain a desired spacing distance between pacing leads 210a and 210b, and the other spacing member 220 can be used for fixation by including deployable anchorage features. In some embodiments, a biocompatible adhesive can be deployed to releasably adhere at least some portions of pacing lead 200 and/or ancillary device 230 to the epicardial surface. In some embodiments, an additional stabilizing arm (e.g., as shown in FIG. 4) is utilized to hold the pacing lead 200 and/or ancillary device 230 in place acutely, and the stabilizing arm becomes resorbed over time as the pacing lead 200 and/or ancillary device 230 becomes fibrosed in place.

In other embodiments, one or more lumens of steerable sheath 120 can be used for additional purposes. Such purposes can include, but are not limited to, aspiration, irrigation, insufflation, delivery of pacing leads, delivery of ultrasound devices, delivery of direct visualization devices, delivery of echocardiography devices, delivery of agents (e.g., steroids, stem cells, etc.), and the like.

Figure 3D:
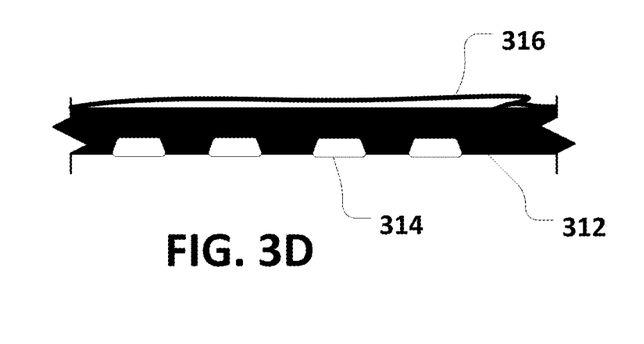
FIG. 3D is a side view of a portion of a pacing lead that includes a stabilization member shown in a retracted configuration.
Figure 3E:
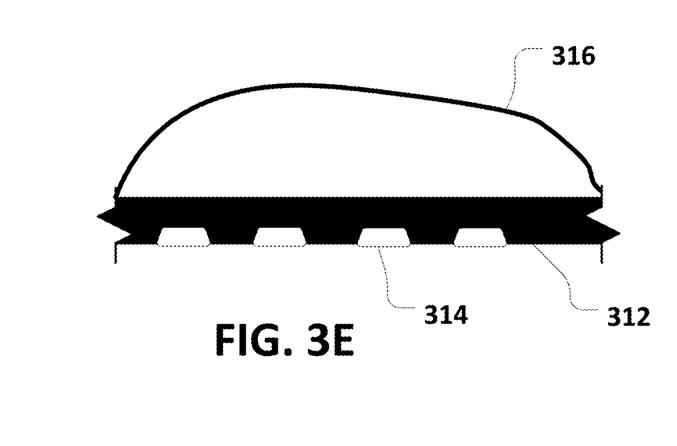
FIG. 3E is the pacing lead portion of FIG. 3D showing the stabilization member in an extended configuration.
Figure 3F:
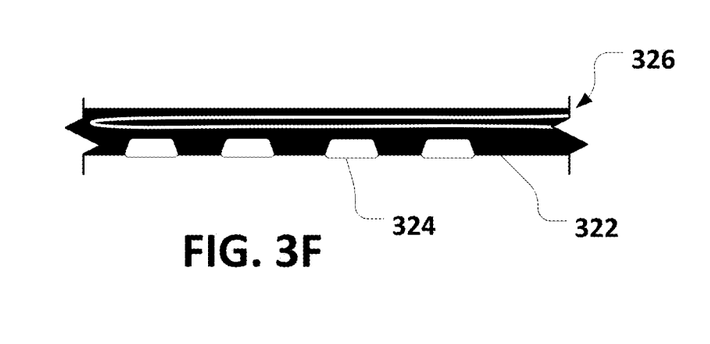
FIG. 3F is a side view of a portion of a pacing lead that includes a cooling manifold.
Figure 3G:
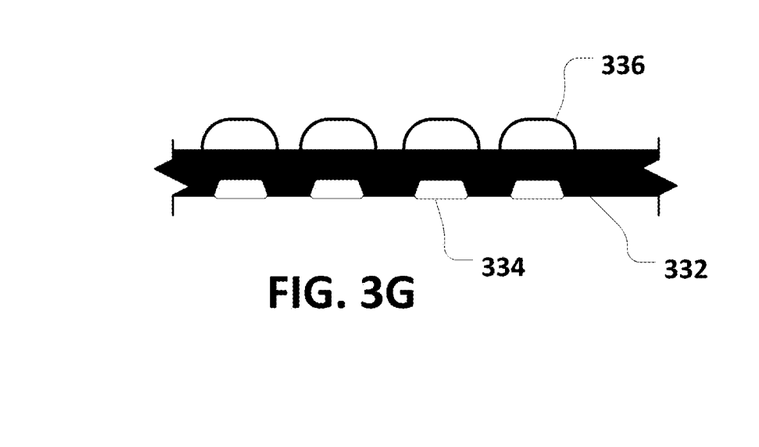
FIG. 3G is a side view of a portion of a pacing lead that includes multiple stabilization members.

FIGS. 3D-3G illustrate optional features that can be included on any of the pacing leads provided herein, alone or in combinations thereof. FIG. 3D is a side view of a portion of a pacing lead 312 (with electrodes 314) that includes a stabilization member 316 shown in a retracted configuration. FIG. 3E shows the pacing lead portion 312 of FIG. 3D with the stabilization member 316 in an extended configuration so as to provide a stabilization force. FIG. 3F is a side view of a portion of a pacing lead 322 (with electrodes 324) that includes a cooling manifold 326. FIG. 3G is a side view of a portion of a pacing lead 332 (with electrodes 334) that includes multiple stabilization members 336.

Stabilization member 316 and/or stabilization members 336 can have a variety of different types of construction. For example, stabilization member 316 and/or stabilization members 336 can be a balloon member, a mesh body, a wire member, and the like. Stabilizing member 316 and/or stabilization members 336 can be used to separate the pericardial sac from the myocardium, and to provide normal force to facilitate integrity of contact between pacing lead 312 and/or pacing lead 332 with the myocardium. Such spacing can provide enhanced isolation of electrical fields emanating from pacing lead 312 and/or pacing lead 332, to prevent or substantially inhibit extracardiac stimulation therefrom, or during ablation to provide protection to surrounding tissue, both for use in the pericardium and other potential applications detailed earlier.

Cooling manifold 326 is a tubular channel through which a cooling fluid (liquid or gas) can flow to cool pacing lead 322. Accordingly, damage from heat generated by electrodes 324 can be prevented or substantially inhibited.

With reference to FIG. 4, bifurcated multi-electrode pacing lead 200 can be used to treat heart 10. It should be understood that, while this device is described in the context of pacing, this device can also be used for other purposes including, but not limited to, ablation, defibrillation, and a combination of pacing and defibrillation.

To arrive at the configuration shown, the distal end portion of steerable delivery sheath 120 is extended through pericardial sac 14 of heart 10 (e.g., refer to FIG. 1). In some implementations, a dilator with a pointed distal tip is initially delivered through a lumen of delivery sheath 120 and used to penetrate pericardial sac 14. After distal end portion of steerable delivery sheath 120 has been positioned inside of pericardial sac 14 and against myocardium 12, first pacing lead 210a and second pacing lead 210b can be extended from the distal end of delivery sheath 120 to rest against myocardium 12. Elongate flexible spacing member 220 can be extended between the distal ends of first pacing lead 210a and second pacing lead 210b so as to create a desired spacing between first pacing lead 210a and second pacing lead 210b. One or more radiopaque markers on delivery sheath, and/or first pacing lead 210a and second pacing lead 210b can assist the clinician using fluoroscopy to achieve a desired positioning, orientation, and configuration of the bifurcated multi-electrode pacing lead 200.

While in the depicted embodiment spacing member 220 extends between the extreme distal ends of first pacing lead 210a and second pacing lead 210b, in some embodiments spacing member 220 is positioned between first pacing lead 210a and second pacing lead 210b at various other locations that are not at the extreme distal ends thereof. That is, in some embodiments spacing member 220 extends between first pacing lead 210a and second pacing lead 210b at locations proximal of the extreme distal ends, such as near the midpoints of first pacing lead 210a and second pacing lead 210b, for example. Other locations are also envisioned. In some embodiments, more than one spacing member 220 is included. For example, two or more spacing members 220 at different locations between first pacing lead 210a and second pacing lead 210b can be included in some embodiments. In some embodiments, one or more electrodes are included on the one or more spacing members 220.

In some embodiments, a stabilizing member 240 is included as part of bifurcated multi-electrode pacing lead 200. In some embodiments, two or more stabilizing members 240 located at various positions in relation to first pacing lead 210a and second pacing lead 210b are included. In some embodiments, one or more electrodes are included on one or more stabilizing members 240. Stabilizing member 240 can be used to separate pericardial sac 14 from myocardium 12, and to provide normal force to facilitate integrity of contact between first pacing lead 210a and second pacing lead 210b with myocardium 12. Such spacing can facilitate movability of bifurcated multi-electrode pacing lead 200 within pericardial sac 14, and can provide enhanced isolation of electrical fields emanating from first pacing lead 210a and second pacing lead 210b, to prevent or substantially inhibit extracardiac stimulation therefrom.

In some embodiments, stabilizing member 240 may also have pacing electrodes attached. In some such embodiments, such electrodes may be useful for pacing phrenic nerve 16 for patients with respiratory disorders or for sensing phrenic nerve activity to adjust pacing rate to provide rate-responsive pacing. In an alternative method for rate-responsive pacing, one of the aforementioned lumens could be used to sense intrapericardial pressure as a marker for respirator rate and/or ventricular dysfunction.

The uninsulated and exposed surfaces of electrodes 214ba, 214bb, 214bc, and 214db (and 214ba, 214bb, 214bc, and 214db on first pacing lead 210a that are not labeled because of space constraints) are orientated to face myocardium 12. Put differently, insulation on electrodes 214aa, 214ab, 214ac, 214ad, 214ba, 214bb, 214bc, and 214bd is orientated to substantially prevent or inhibit electrical fields from emanating away from myocardium 12, such as toward a phrenic nerve 16. In this manner, the electrical fields for pacing that emanate from bifurcated multi-electrode pacing lead 200 are directional, and extracardiac stimulation therefrom is inhibited or substantially prevented.

Figure 5A:
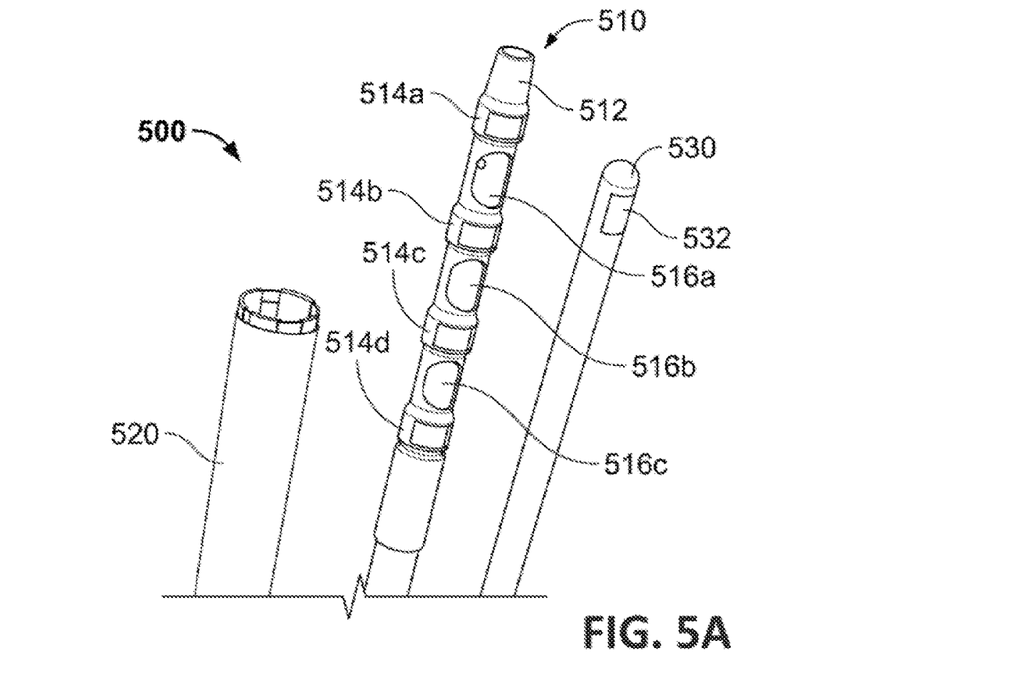
FIG. 5A are perspective views of another embodiment of a multi-electrode pacing lead system in accordance with some embodiments provided herein.
Figure 5B:
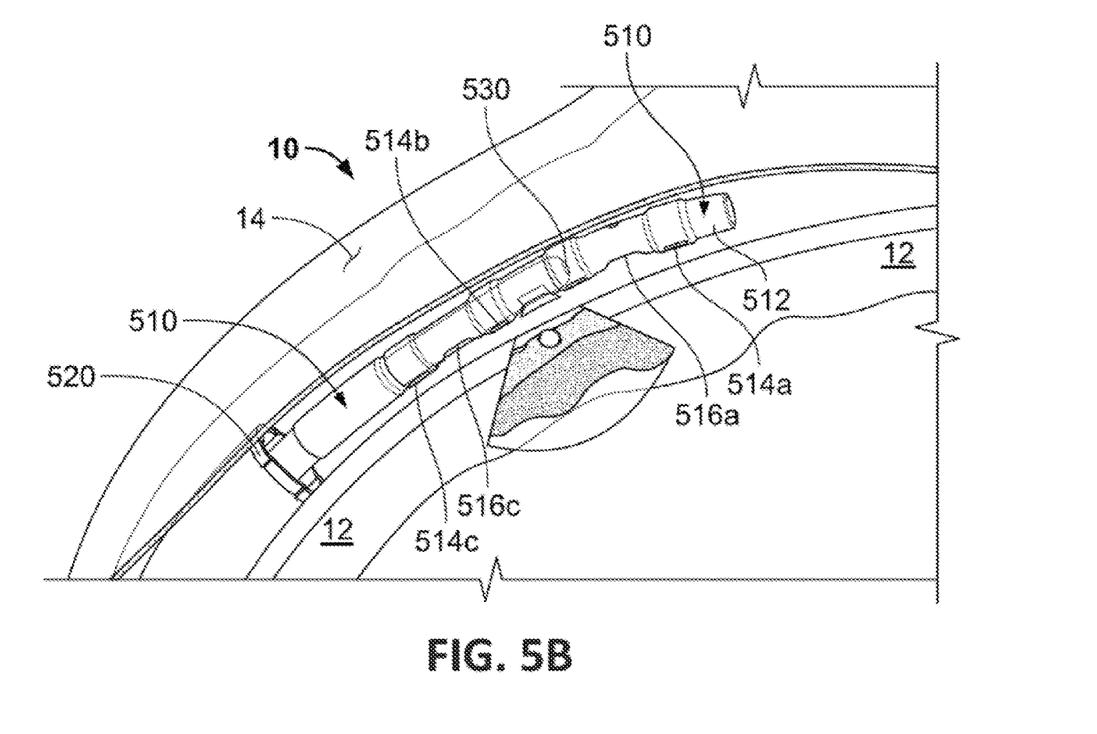
FIG. 5B is a perspective cutaway view of the pacing lead of FIG. 5A positioned within the pericardial sac such that the electrodes of the pacing lead are in contact with myocardial tissue.

With reference to FIGS. 5A and 5B, another example pacing system 500 for epicardial pacing of heart 10 is provided. Pacing system 500 includes a delivery sheath 520 that can be steerable and analogous to sheath 120 in some embodiments, a multi-electrode pacing lead 510, and an imaging catheter 530 that can be an ultrasonic imaging catheter, for example. Pacing lead 510 is slidably disposable within a lumen of delivery sheath 520. Pacing lead 510 includes one or more electrodes 514a, 514b, and 514c, and a distal tip portion 512. Imaging catheter 530 is slidably disposable within a lumen of pacing lead 510. In some embodiments, pacing system 500 also includes one or more radiopaque markers disposed on deliver sheath 520 and/or on pacing lead 510. It should be understood that, while this device is described in the context of pacing, this device can also be used for other purposes including, but not limited to, ablation, defibrillation, and a combination of pacing and defibrillation. In some embodiments, pacing system 500 can be used for atrial-ventricular pacing, multi-site ventricular pacing, or biventricular pacing for CRT.

In some embodiments, pacing lead 510 includes one or more apertures 516a, 516b, and 516c. Apertures 516a, 516b, and 516c are configured to allow an imaging sensor 532 of imaging catheter 530 to project imaging signals therethrough, like a window. Such imaging can take place, in some embodiments, between two of electrodes 514a, 514b, and 514c. The imaging can be performed either and/or both during the use of electrodes 514a, 514b, and 514c, or while electrodes 514a, 514b, and 514c are not in use. Accordingly, imaging catheter 530 can be used to assist a clinician operator to orient pacing lead 510 in relation to heart 10 such that the uninsulated surfaces of electrodes 514a, 514b, and 514c face myocardium 12. In some embodiments, one or more of apertures 516a, 516b, and 516c can additionally, or alternatively, be used for suction or aspiration. Suction may advantageously enhance the physical contact between one or more of electrodes 514a, 514b, and 514c and the epicardial tissue surface in some implementations.

While in the depicted embodiment the cross-sectional shape of pacing lead 510 is generally circular, the circular cross-sectional shape is not required. For example, in some embodiments pacing lead 510 has other cross-sectional shapes including, but not limited to, ovular, elliptical, rectangular, triangular, and the like. In some such embodiments, pacing lead 510 can have a propensity for a certain side of pacing lead 510 to be orientated against tissue, such as myocardium 12.

In some embodiments, portions of electrodes 514a, 514b, and 514c are insulated to substantially prevent or inhibit electrical fields from emanating away from myocardium 12 (in a fashion analogous to electrodes 214aa, 214ab, 214ac, 214ad, 214ba, 214bb, 214bc, and 214bd described above). In that manner, electrodes 514a, 514b, and 514c provide directional electrical fields, and extracardiac stimulation from electrodes 514a, 514b, and 514c can be inhibited or substantially prevented. Electrodes 514a, 514b, and 514c can be used for bipolar or unipolar ablation and/or pacing. Electrodes 514a, 514b, and 514c can be shaped in the various configurations and can have any of the properties as described above in reference to electrodes 214aa, 214ab, 214ac, 214ad, 214ba, 214bb, 214bc, and 214bd, for example.

Figure 6A:
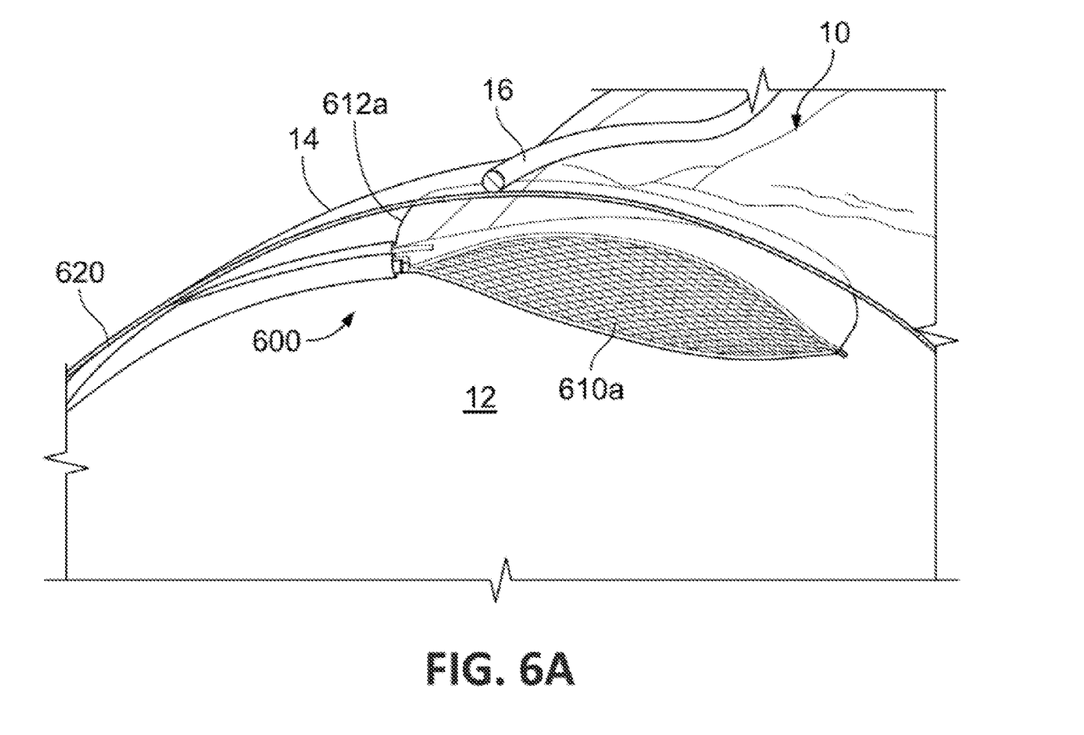
FIGS. 6A and 6B are perspective views of an example embodiment of a ablation system shown in contact with myocardial tissue in accordance with some embodiments provided herein.
Figure 6B:
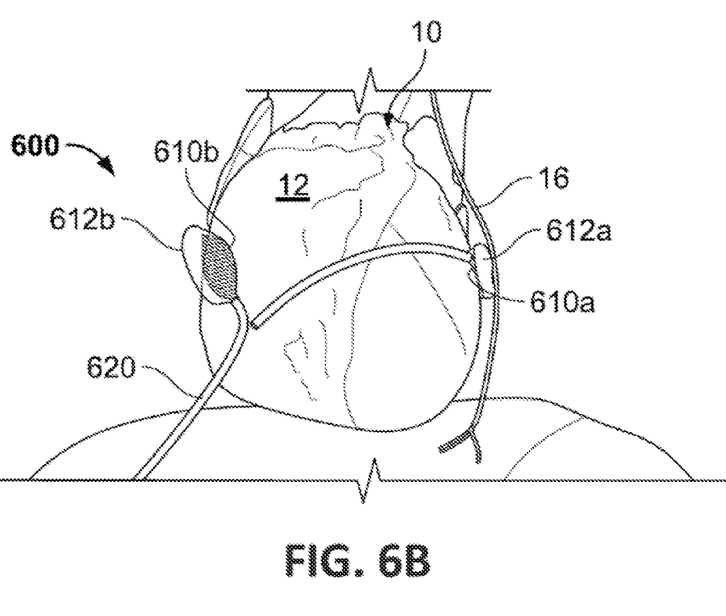

With reference to FIGS. 6A and 6B, an example defibrillation system 600 includes a delivery sheath 620 that can be steerable and analogous to sheath 120 in some embodiments, a first expandable mesh containing an electrode 610a and a second expandable mesh containing an electrode 610b, and a first stabilization member 612a and a second stabilization member 612b. In some embodiments, defibrillation system 600 can alternatively, or additionally, be used for ablation. In some embodiments, both first expandable mesh containing an electrode 610a and second expandable mesh containing an electrode 610b are delivered through one or more lumens of delivery sheath 620. In some embodiments, a second delivery sheath is used and first expandable mesh containing an electrode 610a and second expandable mesh containing an electrode 610b are delivered through separate delivery sheaths.

In some embodiments, first expandable mesh containing an electrode 610a and second expandable mesh containing an electrode 610b are expandable elements comprised of an outer shell made of a conductive expandable mesh material (e.g., nitinol). In some embodiments, first stabilization member 612a and second stabilization member 612b are attached to or are positioned adjacent to first expandable mesh containing an electrode 610a and second expandable mesh containing an electrode 610b. In some embodiments, first stabilization member 612a and second stabilization member 612b are inflatable balloon devices that can press against pericardium 14 and first expandable mesh containing an electrode 610a and second expandable mesh containing an electrode 610b to stabilize first expandable mesh containing an electrode 610a and second expandable mesh containing an electrode 610b.

In some embodiments, the outer shell is made of a non-conductive polymeric expandable mesh material that self-expands to a three dimensional shape such as, but not limited to, a prism, a cylinder, an ellipsoid, and the like. In some embodiments, other materials and other shapes are used. The outer shells can contain one or more electrodes that could be used for pacing, ablation, defibrillation, or a combination thereof. In some embodiments, one or more electrodes can additionally or alternatively be positioned on the exterior of first expandable mesh containing an electrode 610a and second expandable mesh containing an electrode 610b.

The outer shells of first expandable mesh containing an electrode 610a and second expandable mesh containing an electrode 610b act as spacing member to prevent or inhibit direct contact between defibrillation electrodes and pericardium 14. This results in a shocking vector between 610a and 610b with insulation to prevent extra myocardial stimulation. The insulation may be in the form of an inflatable first stabilization member 612a and second stabilization member 612b as depicted in FIG. 6A, or may be another insulative material to directionally guide the current away from extracardiac structures. The use of a mesh or multiple electrodes electrically coupled provide a sufficiently large surface area for defibrillation to prevent direct burns of myocardium 12. The use of fusion imaging will also permit defibrillation electrode positioning relative to cardiac structures or to selectively choose appropriate electrodes to deliver energy.

In some embodiments, defibrillation system 600 is a bipolar defibrillation system. That is, defibrillation energy is made to emanate from one of first expandable mesh containing an electrode 610a or second expandable mesh containing an electrode 610b, and to be received by the other of first expandable mesh containing an electrode 610a or second expandable mesh containing an electrode 610b. In other embodiments, only a single expandable mesh is used and energy passes from that single expandable mesh to another type of electrode, such as an an intravascular electrode(s), or subcutaneous electrode(s). With regards to ablation, the mesh epicardial electrode may also serve as a return electrode for a standard endocardial ablation catheter resulting in full-thickness bipolar ablation without damage to extra-cardiac structures. In some embodiments, the ablation system 600 can perform a full-thickness ablation process from the endocardium to the epicardium.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

For example, it should be understood that while some device embodiments are described above in the context of pacing, those devices can also be used for ablation. In some such ablation implementations, the devices described above can be positioned on the epicardium and one or more other instruments can be positioned within the heart. Ablation energy can be delivered between the instruments such that the energy flows through the myocardium. In addition, any of the devices described herein can be connected to and used in conjunction with a subcutaneous defibrillator or pacing device, as well as an external defibrillator. Further, any of the devices provided herein can be used in conjunction with an autonomic nerve stimulator.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An epicardial pacing lead device comprising:
   a first shaft having one or more electrodes and insulation disposed thereon;
   a second shaft having one or more electrodes and insulation disposed thereon; and
   an elongate flexible spacing member that is slidably disposed in a lumen of either one of the first shaft or the second shaft but not in lumens of both the first and second shafts, and
   wherein at least some of the electrodes are insulated by the insulation so as to inhibit emanation of electrical fields therefrom in a particular direction corresponding to locations of the insulation.

2. The epicardial pacing lead device of claim 1, wherein the first shaft and the second shaft have the same number of electrodes.

3. The epicardial pacing lead device of claim 2, wherein the epicardial pacing lead device is a bipolar epicardial pacing device.

4. The epicardial pacing lead device of claim 1, further comprising a delivery sheath and wherein the first shaft and the second shaft are configured for deployment from one or more lumens defined by the delivery sheath.

5. The epicardial pacing lead device of claim 1, wherein one or more of the electrodes that are insulated by the insulation are each insulated by the insulation so as to inhibit emanation of electrical fields therefrom in a same direction.

6. The epicardial pacing lead device of claim 1, wherein the first shaft and the second shaft are distinctly separate distal end portions extending from a common shaft such that the separate distal end portions and the common shaft comprise a Y-shape.

7. The epicardial pacing lead device of claim 1, wherein distal end portions of the first shaft and the second shaft are interconnected by the elongate flexible spacing member.

8. The epicardial pacing lead device of claim 7, wherein the elongate flexible spacing member is movable by a clinician operator relative to only one of the first shaft and the second shaft to: (i) draw the distal end portions of the first shaft and the second shaft towards each other and (ii) separate the distal end portions of the first shaft and the second shaft away from each other.

9. The epicardial pacing lead device of claim 7, wherein the elongate flexible spacing member is a first elongate flexible spacing member, and further comprising a second elongate flexible spacing member interconnecting the first shaft and the second shaft, and wherein the second elongate flexible spacing member is located proximally of the first elongate flexible spacing member.

10. The epicardial pacing lead device of claim 1, further comprising a stabilization member interconnecting the first shaft and the second shaft, and wherein the stabilizing member projects away from a plane defined by the first shaft in combination with the second shaft.

11. The epicardial pacing lead device of claim 1, further comprising an ancillary device that is slidably deliverable through the delivery sheath, and wherein the ancillary device includes an anchoring member.

12. An epicardial pacing device system comprising:
    an epicardial pacing lead device comprising a shaft defining a lumen and having one or more electrodes and insulation disposed thereon, wherein at least some of the electrodes are insulated by the insulation so as to inhibit emanation of electrical fields therefrom in a particular direction corresponding to locations of the insulation, wherein the epicardial pacing lead device defines at least one aperture spaced between two adjacent electrodes of the one or more electrodes;
    an imaging catheter that is slidably disposable within the lumen of the shaft, the imaging catheter including an imaging sensor sized for performing imaging through the at least one aperture; and
    a delivery sheath, wherein a first lumen of the delivery sheath is configured to slidably receive the epicardial pacing lead device.

13. The epicardial pacing device system of claim 12, wherein at least a distal end portion of the delivery sheath is steerable.

14. The epicardial pacing device system of claim 12, wherein at least a distal end of the shaft is steerable.

* * * * *